United States Patent [19]
Linden

[11] Patent Number: 5,609,603
[45] Date of Patent: Mar. 11, 1997

[54] SURGICAL CUTTING DEVICE WITH SAFETY INTERLOCK

[75] Inventor: Harry A. Linden, Santa Barbara, Calif.

[73] Assignee: Hall Surgical Div. of Zimmer Inc., Carpenteria, Calif.

[21] Appl. No.: 641,292

[22] Filed: Apr. 30, 1996

Related U.S. Application Data

[63] Continuation of Ser. No. 355,387, Dec. 13, 1994, abandoned.

[51] Int. Cl.⁶ .................................................. A61B 17/14
[52] U.S. Cl. ............................. 606/177; 279/75; 279/905
[58] Field of Search ........................... 606/82, 176, 177, 606/178, 179; 30/392, 394; 279/75, 905

[56] References Cited

U.S. PATENT DOCUMENTS

| | | | |
|---|---|---|---|
| 3,521,895 | 7/1970 | Smith | 279/75 |
| 4,131,165 | 12/1978 | Wanner et al. | 279/75 X |
| 4,204,692 | 5/1980 | Hoffman | 279/81 |
| 4,285,129 | 8/1981 | Hoffman | 30/392 |
| 4,298,074 | 11/1981 | Mattchen | 173/129 |
| 4,299,402 | 11/1981 | Hoffman | 279/75 |
| 5,112,299 | 5/1992 | Pascaloff | 604/22 |
| 5,222,956 | 6/1993 | Waldron | 606/79 |
| 5,304,191 | 4/1994 | Gosselin | 606/172 |
| 5,340,129 | 8/1994 | Wright | 606/177 X |
| 5,437,465 | 8/1995 | Vögele et al. | 279/75 X |

OTHER PUBLICATIONS

"The Hall Versipower Sternum Saw Instruction Manual", by Zimmer, 1991 Lit. No. HS 22–17446–00, 24 Pages.
"The Hall Thoracic Surgery System" Precision, Power and Control for Sternotomies, by Zimmer, 1991, 6 Pages.

Primary Examiner—Michael Powell Buiz
Assistant Examiner—Patrick W. Rasche
Attorney, Agent, or Firm—Gene Warzecha

[57] ABSTRACT

A surgical cutting device having a powered handpiece adapted to receive a cutting blade. The cutting blade is locked to the drive shaft by a locking ball holding member which is locked in place by a cylindrical cam ring which urges the balls of the locking device into corresponding notches in the blade. A second locking ball holding member is provided on the housing of the handpiece to lock the cylindrical cam ring itself. A blade guard extends from the cylindrical cam ring to produce a surgical cutting device having an improved safety feature which prevents its operation without the guard in proper position.

10 Claims, 5 Drawing Sheets

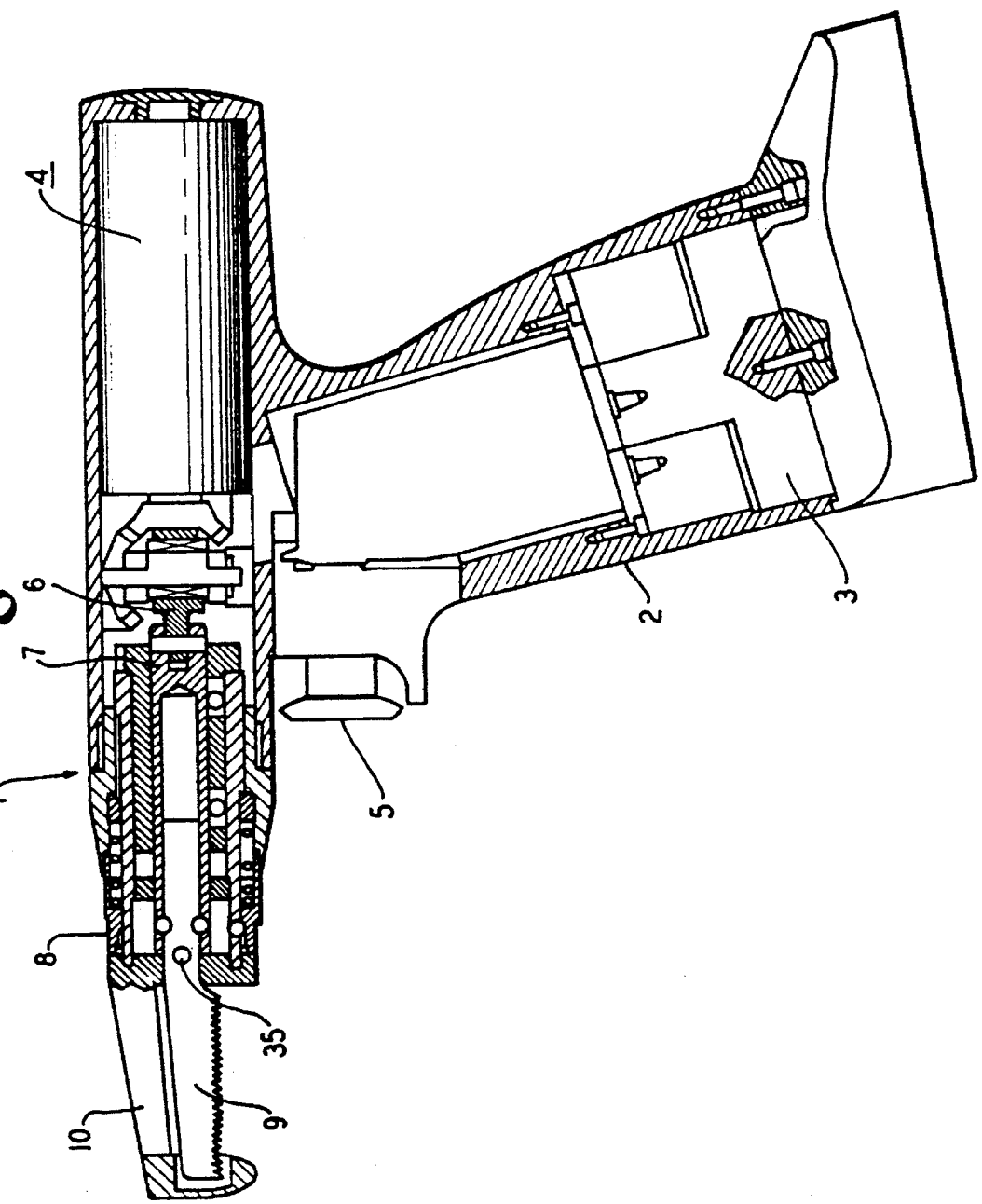

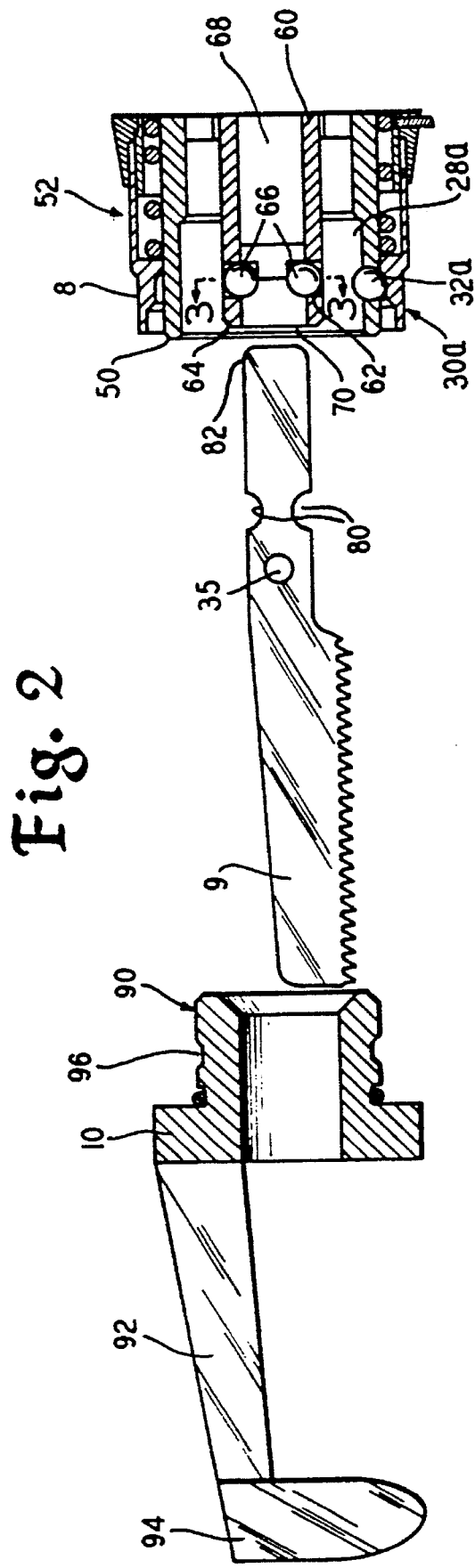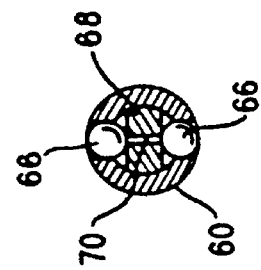

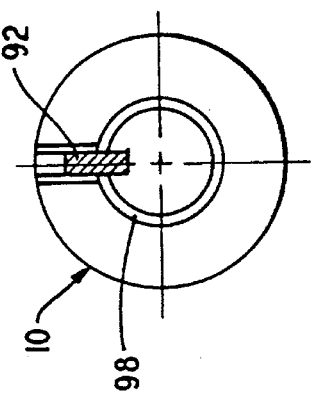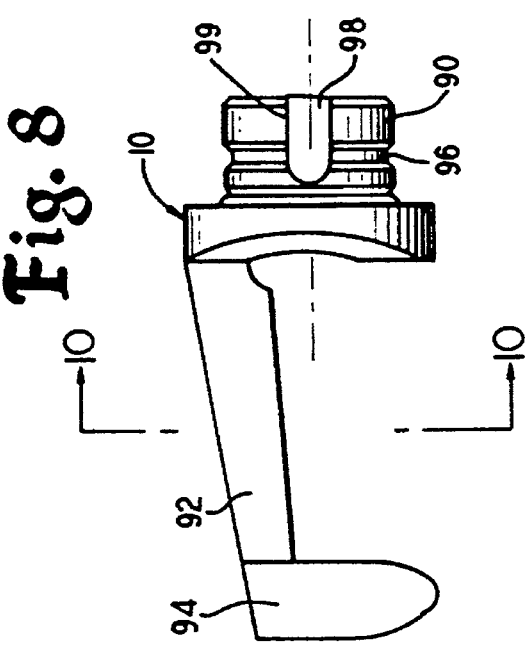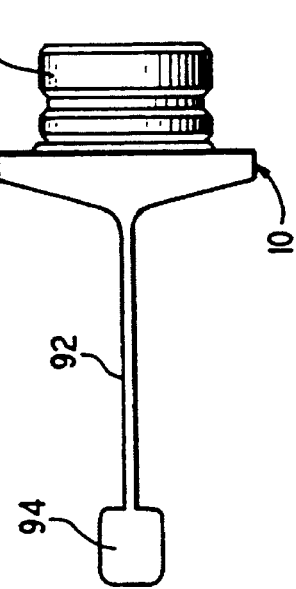

SURGICAL CUTTING DEVICE WITH SAFETY INTERLOCK

This is a continuation application of application Ser. No. 08/355,387, filed Dec. 13, 1994 now abandoned.

BACKGROUND OF THE INVENTION

1. Field of the Invention

This invention relates generally to powered surgical cutting devices. More particularly, this invention relates to powered surgical blades and means for joining these blades to a surgical handpiece. Still more particularly, this invention relates to a powered sternum saw provided with a guard and a safety interlock to prevent operation of the saw unless all parts are properly assembled.

2. Description of the Prior Art

Surgical saws are well known for cutting various types of tissue during surgical procedures. The saws are often provided with shields or guards to prevent inadvertent damage to tissue adjacent the surgical work site. Such guards are particularly important when using powered surgical saws.

One type of known surgical cutting device is a sternum saw which is, as the name implies, used for cutting through the sternum during a surgical procedure. A collet mechanism is provided to secure the reciprocating saw blade to the handpiece and the collet nut is tightened with a wrench or other tool in order to hold the flat "saber saw" in a longitudinally reciprocating drive shaft. The collet not only grips the saw blade but also acts to squeeze a locking alignment ball into a hole formed in the proximal end of the blade in order to prevent the blade from falling out of the handpiece should the collet become loose. Because of the sensitive location of the sternum such surgical saws are generally provided with a saw blade guard in order to partially enclose the reciprocating saw blade to preclude it from accidentally cutting unintended tissue. However, the presence of the guard limits access to the collet nut and makes it more difficult to tighten the blade. Additionally, the need to keep track of a separate tool or wrench to tighten the collet adds to the difficulty. Improvements in design are desirable to facilitate the assembly of the blade onto the handpiece. In addition to facilitating attachment of the saw blade to the handpiece, it is always desirable to incorporate additional safety features in powered surgical saws. Consequently, it is an object of this invention to provide a safety interlock which requires all components of the powered surgical saw to be properly assembled before the saw can effectively cut tissue.

It is another object of this invention to provide a sternum saw with a sternum safety guard which necessarily has to be in proper position in order to enable operation of the saw.

It is also an object of this invention to produce a powered surgical saw with a means for attaching the saw blade to the handpiece without using an extra tool. Such a handpiece will be sometimes referred to as a "wrench-less" handpiece.

It is yet another object of this invention to produce, in a powered surgical saw, a safety interlock which simultaneously locks and properly positions a blade and a blade guard.

SUMMARY OF THE INVENTION

These and other objects of this invention are achieved by the preferred embodiment disclosed herein which is a surgical saw for use with an elongated surgical blade having a proximal end, a distal end and at least one notch detent at the proximal end. The saw comprises a housing or handpiece having an opening at its distal end and a drive shaft having an end adjacent the opening for receiving the surgical blade. The handpiece includes a means for driving the drive shaft. A blade receiving means at the end of the drive shaft comprises a first locking-ball holding means situated on the drive shaft for holding the proximal end of the surgical blade. The balls of the first locking-ball holding means are held in the notch of the surgical blade by a cylindrical cam ring attached to the base of the blade guard. An outer surface of the cam ring is provided with an annular groove which operates with the balls of a second locking-ball holding means situated on the handpiece. A cylindrical collar means on the handpiece holds the balls of the second locking-ball holding means in the annular groove and thereby locks the blade and the guard in proper position.

The invention is also embodied in the method of connecting a surgical cutting blade to a power source for driving the device. The method comprises the steps of providing a surgical cutting device having a notch detent at its proximal end, providing a first locking-ball holding means to hold the device to the power source and holding the cutting device and the first locking-ball holding means in locked position with a cam ring which is itself locked in place by a second locking-ball holding means.

BRIEF DESCRIPTION OF THE DRAWINGS

FIG. 1 is a cross-sectional view of a sternum saw constructed in accordance with the principles of this invention.

FIG. 2 is an exploded diagrammatic view of the distal end of FIG. 1.

FIG. 3 is a cross-sectional view of FIG. 2 taken along the line 3—3.

FIG. 8 is a side elevation view of the saw guard of FIG. 1.

FIG. 9 is a top plan view of FIG. 8.

FIG. 10 is a view of FIG. 8 taken along the line 10—10.

DESCRIPTION OF THE PREFERRED EMBODIMENT

Figure 4:
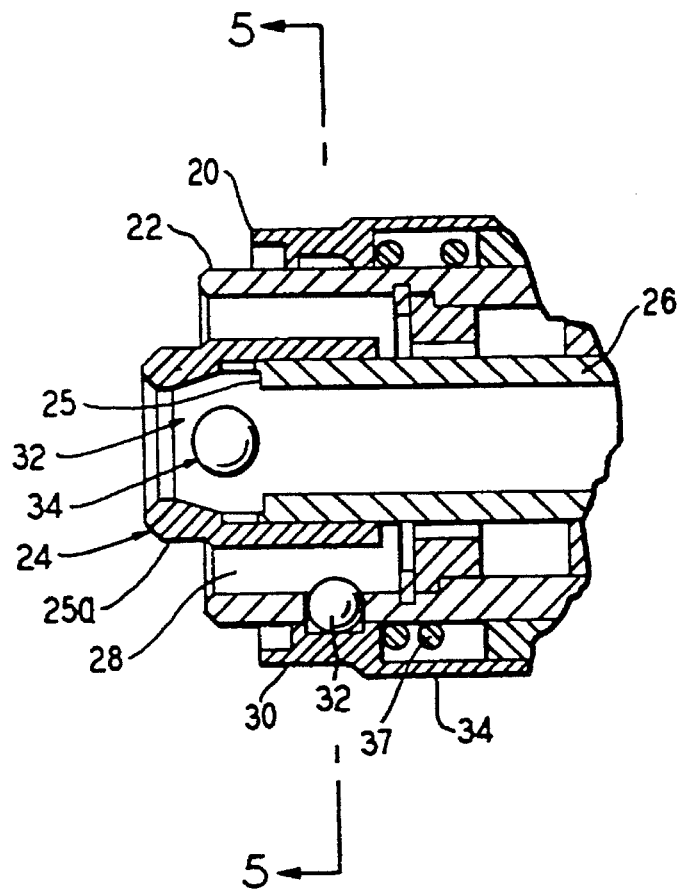
FIG. 4 is a cut-away cross-sectional side elevation view of a portion of the distal end of a prior art surgical saw showing a known collet mechanism for holding a saw blade.

Referring now to FIGS. 1 and 2, powered surgical saw 1 is shown comprising a "wrench-less" handpiece 2 having a battery receptacle 3 (to receive a battery, not shown), motor 4, trigger 5, motor output shaft 6, drive shaft 7 and a distal working end 8 to which a sternum saw blade 9 and guard 10 are attached. Most of the foregoing components are conventional and form no part of this invention. The invention relates to the distal end 8 and the manner in which blade 9 and guard 10 are attached to handpiece 2.

Figure 5:
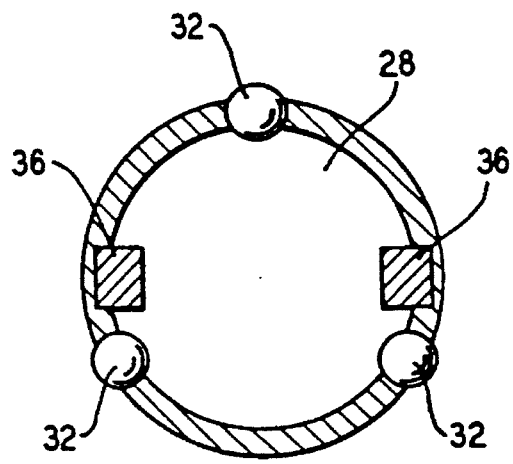
FIG. 5 is a cross-sectional view of FIG. 4 taken along the line 5—5.

For comparison and explanatory purposes, the distal end 20 of a prior art handpiece is shown in FIG. 4. It will be understood that the distal end 8 of handpiece 2 in FIG. 1 is comparable in function to prior art distal end 20 and, therefore, the proximal end of handpiece 2 (to the right of distal end 8 in FIG. 1) may be used in a prior art handpiece to drive distal end 20. The prior art distal end 20 comprises a collet/output shaft assembly 22 having a blade receiving collet 24 threaded on the distal end of drive shaft 26, an annular, guard receiving chamber 28 surrounding collet 24 and a guard locking mechanism 30. Blade receiving collet 24 comprises a threaded collet tip 25 provided with a nut 25A, a flat, blade receiving opening 32 (in the plane of the paper) and a ball 34 intended to be received within a corresponding alignment aperture 35 of a surgical saw blade. As will be understood below, one advantage of the invention is that saw blades made for use with the new "wrench-less" handpiece may continue to include alignment aperture 35 for use with a prior art handpiece (depending on user preference). Collet 24 is operated in a conventional manner by being tightened by the turning of the nut to clamp and frictionally engage the saw blade. Annular guard receiving chamber 28 is provided to receive the base of a sternum guard similar to that shown in FIGS. 1 and 2 and in greater detail in FIGS. 8–10. The guard is retained in chamber 28 by locking mechanism 30 which relies on the interaction of three annularly spaced locking balls 32 with a cam ring in the form of retractable, spring-loaded, cylindrical locking collar 34 in a conventional manner. Spring 37 urges collar 34 distally to lock balls 32 within an associated annular groove of the base of the guard. As best seen in FIGS. 4 and 5, annular chamber 28 is provided with three locking balls 32 and a pair of diametrically opposed keys 36 in order to properly orient the guard relative to the blade as will be understood below. It should be noted that the prior art collet/output shaft assembly 22 operates independently of locking mechanism 30. As will be understood, the invention described below makes proper functioning of a new collet/output shaft assembly dependent upon the guard locking mechanism.

Figure 6:
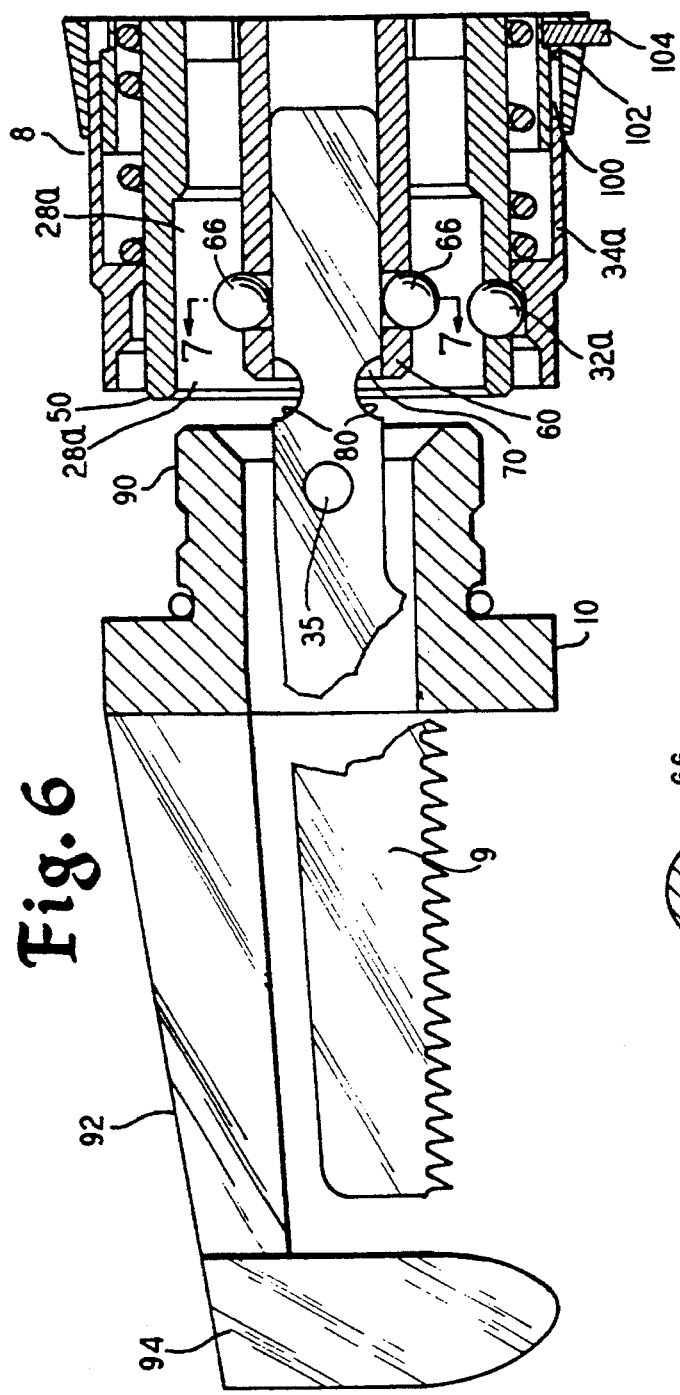
FIG. 6 is a view of FIG. 2 showing the components partially assembled.

The invention will now be described with reference to a new collet/output shaft assembly 50 best seen in FIGS. 1, 2, 6 and 7. The invention produces a "wrench-less" design by enabling a slightly modified guard and saw blade to be attached to a handpiece without the use of any auxiliary tools to tighten a collet as in the prior art device. In FIG. 2, the distal end 52 of collet/output shaft assembly 50 is shown in exploded association with saw blade 9 and guard 10. In FIG. 6, the components are shown partially assembled to show the operation of the safety locking mechanism. The proximal portion of collet/output shaft assembly 50 (not shown) is similar to that of prior art collet/output shaft assembly 22 and does not need to be described to understand the present invention.

Collet/output shaft assembly 50 comprises a reciprocating cylindrical drive shaft 60 provided with an inner locking ball retaining mechanism 62 near its distal end 64. Locking ball retaining mechanism 62 comprises a pair of diametrically opposed retaining balls 66 situated in restricted apertures in drive shaft 60 in a conventional manner. A ball retaining insert 68 is provided to prevent the balls from falling into the interior of drive shaft 60 when blade 9 is not in position. The distal end of insert 68 is provided with a diametrical slit 70 designed to receive the proximal end of flat blade 9 in aligned orientation relative to balls 66.

Saw blade 9 and guard 10 are slightly modified versions of the prior art components in order to enable them to work in the invention hereof. Blade 9 is a conventional saber saw type reciprocating surgical blade modified by having notches 80 formed on opposite sides of the blade shaft. Aperture 35, best seen in FIG. 2, is used in blade 9 even though it has no function in the invention and is only provided to make blade 9 usable in prior art handpieces. Notches 80 are spaced a predetermined distance distally from the proximal end 82 of blade 9 and, as will be understood below, are intended to receive balls 66 when blade 9 is properly seated within collet/output shaft assembly 50.

Guard 10, best seen in FIGS. 8–10, comprises a ball locking cam in the form of cylindrical cam ring base portion 90, a connecting arm 92 and a slotted, distal guard head 94. Cylindrical base 90 has an outer diameter adapted to fit annular chamber 28a surrounding the distal end of drive shaft 60 and includes in its outer surface an annular groove 96 which is adapted to receive locking balls 32a of locking mechanism 30a. A pair of diametrically opposed keyways 99 (only one of which is seen in FIG. 8) is provided to engage keys 36 (best seen in FIG. 5). A cylindrical insert 98 is utilized to modify the prior art guard design to assure the inside diameter of base 90 is approximately equal to the outside diameter of shaft 60. The inner surface insert 98 serves as a bearing surface for balls 66 during operation of the saw. Alternatively, the guard base could be made as an integral piece having the appropriate inner diameter. The locking ball retaining mechanism 30a of collet/output shaft 52 is essentially identical to the locking ball retaining mechanism 30 of the prior art device shown in FIG. 4.

Figure 7:
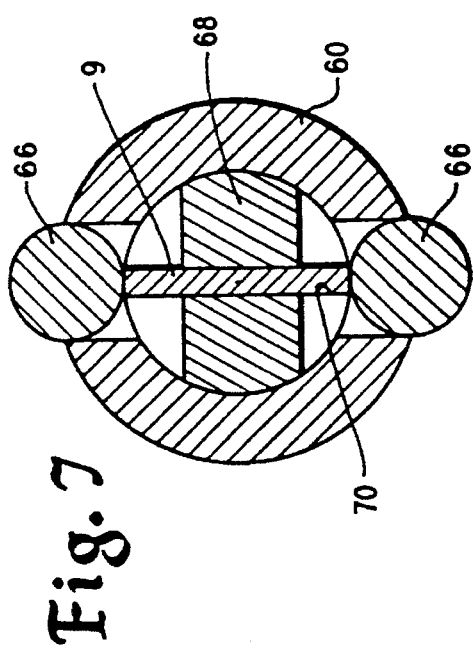
FIG. 7 is a cross-sectional view of FIG. 6 taken along the line 7—7.

It will be understood that as the components shown in FIG. 2 are assembled together, with blade 9 first being inserted into slot 70 at the end of drive shaft 60, balls 66 are pushed radially outwardly as best seen in FIGS. 6 and 7 into guard receiving chamber 28a by the opposed lateral edges o the proximal end of blade 9. When the blade is fully pushed into proper position as best seen in FIG. 1, balls 66 will fall into notches 80. Once the blade is thus properly positioned, tie base 90 of guard 10 will be able to be inserted into guard receiving chamber 28a. If blade 9 is not properly positioned, balls 66 will interfere with the guard and prevent base 90 from fully entering annular chamber 28a. When guard 10 is fully seated outer balls 32a will fall into annular groove 96 in order to lock guard 10 within distal end 8 while enabling the collet/output shaft assembly 50 to reciprocate. It will be understood that the action of locking guard 10 within chamber 28a also locks blade 9 by virtue of trapping balls 66 in notches 80. The base of guard 10, therefore, is essentially an intermediate cam surface acting upon both the blade and the guard locking mechanism.

While the invention is disclosed with respect to a surgical cutting device in the form of a flat and reciprocating saber type saw blade, other modifications of the invention may be made to make it suitable for other types of cutting blades with or without associated guard devices. For example, the invention may be adaptable to rotating arthroscopic shavers having elongated, relatively rotating surgical shaver blades.

As an additional safety feature (best seen in FIG. 6) the cylindrical locking ring 34a may be provided with a notch 100 in its proximal annular edge 102 and the body of distal end 8 of the handpiece could be provided with a radially outwardly extending pin 104. The longitudinal placement of pin 104 is such that ring 34a must be rotated to align notch 100 with pin 1,)4 in order to enable ring 34a to be retracted.

It will be understood that numerous other improvements herein without departing from the spirit and /scope of the and modifications may be made to the preferred embodiment disclosed invention.

What is claimed is:

1. A surgical saw system comprising:

an elongated surgical blade having a proximal end, a distal end and at least one notch detent at the proximal end;

a housing having an opening for receiving said surgical blade;

a drive shaft having an end adjacent said opening;

means for driving said drive shaft;

blade receiving means at the end of said drive shaft for receiving said surgical blade, said blade receiving means comprising a first locking-ball retaining means having at least one ball situated on said drive shaft adjacent said end thereof for engaging said at least one notch at said proximal end of said surgical blade;

a first, unitary cylindrical cam ring means for cooperative engagement with said first locking-ball retaining means, said first, unitary cylindrical cam ring means comprising an inner surface for urging said at least one ball of said first locking-ball retaining means into said at least one notch of said surgical blade, and an outer surface provided with an annular groove;

cam ring receiving means for receiving said first, unitary cylindrical cam ring means, said cam ring receiving means comprising a second locking-ball retaining means having at least one ball situated on said housing for engaging said annular groove;

a second cylindrical cam ring means movably situated on said housing for cooperative engagement with said second locking-ball retaining means, said second cylindrical cam ring means comprising a collar having an inner surface for urging said at least one ball of said second locking-ball retaining means into said annular groove; and means to hold said second cylindrical cam ring means fixed to thereby hold said at least one ball of said second locking-ball retaining means in said annular groove.

2. A surgical saw according to claim 1 further comprising:

an elongated blade guard fixedly attached to and extending distally from said first cylindrical cam ring means.

3. A surgical saw for use with an elongated surgical cutting device having at least one notch at one end thereof, said surgical saw having a housing and a drive shaft within said housing, said drive shaft provided with a receiving means at an end thereof for receiving said surgical cutting device, comprising:

a first plurality of locking balls and corresponding ball-receiving apertures spaced about the drive shaft adjacent said end;

aperture means in said end of said drive shaft for receiving said surgical cutting device in alignment with said drive shaft, said device adapted to be inserted into said drive shaft to juxtapose said at least one notch adjacent and on the radially inner side of said locking balls and ball-receiving apertures;

a cutting device guard means comprising a distal guard portion, a cam lock cylindrical body portion and a longitudinally extending connecting guard portion joining said distal guard portion and said cam lock cylindrical body portion, said cam lock cylindrical body portion having an inner surface adapted to be received adjacent said drive shaft to be juxtaposed on the radially outer side of said locking balls and ball-receiving apertures;

a holding means for securing said cam lock cylindrical body portion to thereby lock said cutting device and guard in place.

4. A surgical saw according to claim 3 wherein said drive shaft is provided with two diametrically opposed locking balls and ball-receiving apertures.

5. A surgical saw according to claim 3 wherein said drive shaft is longitudinally reciprocable when said cam lock cylindrical body portion is in place.

6. A surgical saw according to claim 3 wherein said holding means comprises:

a second plurality of locking balls and corresponding ball receiving apertures spaced about said housing; and ball receiving means on said cam lock cylindrical body portion.

7. A method of connecting a surgical cutting device to a power source having a drive shaft for driving the surgical cutting device comprising the steps of:

providing an elongated surgical cutting device having at least one notch detent at its proximal end;

providing a first locking-ball holding means for holding said cutting device relative to the drive shaft;

placing said at least one notch detent of said cutting device adjacent said first locking-ball holding means to nest at least one ball thereof into said at least one notch detent;

locking said first locking-ball holding means to said at least one notch with a unitary locking cam;

providing a second locking-ball holding means for holding said unitary locking cam relative to said housing; and locking said unitary locking cam with said second locking-ball holding means.

8. A method according to claim 7 wherein the step of locking said first locking-ball holding means enables said at least one ball of said first locking-ball holding means to move to facilitate longitudinally reciprocal motion of said drive shaft.

9. A method according to claim 7 wherein the step of providing an elongated surgical cutting device having at least one notch at its proximal end further comprises the step of providing a flat blade having a pair of notches in opposing, longitudinally extending edges.

10. A surgical saw for use with an elongated surgical cutting device having at least one notch detent at one end thereof, said surgical saw having a housing and a drive shaft, said drive shaft provided with a receiving means at an end thereof for receiving said surgical cutting device, comprising:

a radially inner, first locking-ball retaining means for releasably retaining said elongated cutting device to and in alignment with said drive shaft, said first locking ball retaining means comprising a plurality of locking balls and corresponding ball-receiving apertures spaced about said drive shaft;

a cutting device guard for surrounding a predetermined portion of said elongated cutting device, said guard provided with a cylindrical base portion;

a radially outer, second locking-ball retaining means for releasably retaining said guard to said housing, said second locking-ball retaining means comprising a plurality of locking balls and corresponding ball-receiving apertures spaced about said housing;

an intermediate cylindrical cam surface means interposed between said cylindrical base portion and said drive shaft for simultaneously locking said first locking-ball retaining means to secure said surgical cutting device to said drive shaft and providing means cooperative with said second locking-ball retaining means to secure said cylindrical base portion to said housing.

* * * * *